United States Patent
Guiraudon et al.

[11] Patent Number: 5,364,337
[45] Date of Patent: Nov. 15, 1994

[54] MUSCLE POWERED CARDIAC ASSIST SYSTEM

[75] Inventors: Gerard M. Guiraudon, London, Canada; Ivan Bourgeois, Verviers,

[73] Assignee: Medtronic, Inc., Minneapolis, Minn.

[21] Appl. No.: 47,722

[22] Filed: Apr. 14, 1993

Related U.S. Application Data

[63] Continuation of Ser. No. 597,316, Oct. 15, 1990, Pat. No. 5,205,810.

[51] Int. Cl.$^5$ .............................................. A61M 1/12
[52] U.S. Cl. ........................................... 600/16; 623/3
[58] Field of Search ........................ 600/16, 17; 623/3

[56] References Cited

U.S. PATENT DOCUMENTS

| | | | |
|---|---|---|---|
| 3,595,242 | 7/1971 | Berkovits | 128/421 |
| 3,902,501 | 9/1975 | Citron et al. | 128/418 |
| 4,143,661 | 3/1979 | LaForge et al. | 128/419 |
| 4,312,355 | 6/1982 | Funke | 128/419 |
| 4,384,829 | 5/1983 | Conley et al. | 417/412 |
| 4,411,268 | 10/1983 | Cox | 128/421 |
| 4,453,537 | 6/1984 | Spitzer | 128/1 D |
| 4,457,673 | 7/1984 | Conley et al. | 417/412 |
| 4,666,443 | 5/1987 | Portner | 623/3 |
| 4,771,765 | 9/1988 | Choy et al. | 600/18 |
| 4,813,952 | 3/1989 | Khalafalla | 623/3 |
| 4,919,661 | 4/1990 | Gibney | 623/3 |
| 4,957,477 | 9/1990 | Lundback | 600/16 |
| 4,968,293 | 11/1990 | Nelson | 600/16 |
| 5,007,927 | 4/1991 | Badylak et al. | 623/3 |

Primary Examiner—William E. Kamm
Assistant Examiner—Kennedy J. Schaetzle
Attorney, Agent, or Firm—Harold R. Patton

[57] ABSTRACT

A method and apparatus for providing assistance to a patient's heart using a surgically prepared skeletal muscle. A skeletal muscle, such as the latissimus dorsi, is carefully separated from the skeletal structure leaving enervation and vascularization in tact. The muscle tissue is then separated into two independent contractile masses. Alternatively, two separate skeletal muscles may be used. The first of these is wrapped about the atria. The second is wrapped about the ventricles. Each muscle mass is individually stimulated using an implantable pulse generator. Stimulation to the muscle mass is synchronized to the naturally or artificially paced contractions of the heart to provide the maximum in assistance. During each complete heart cycle, the muscle mass assisting the ventricles is stimulated at the same time as contraction of the ventricular myocardium. The muscle mass assisting the atria is then stimulated at the same time as contraction of the atrial myocardium. Various sensing and stimulating modes may be used to optimize cardiac assistance.

4 Claims, 6 Drawing Sheets

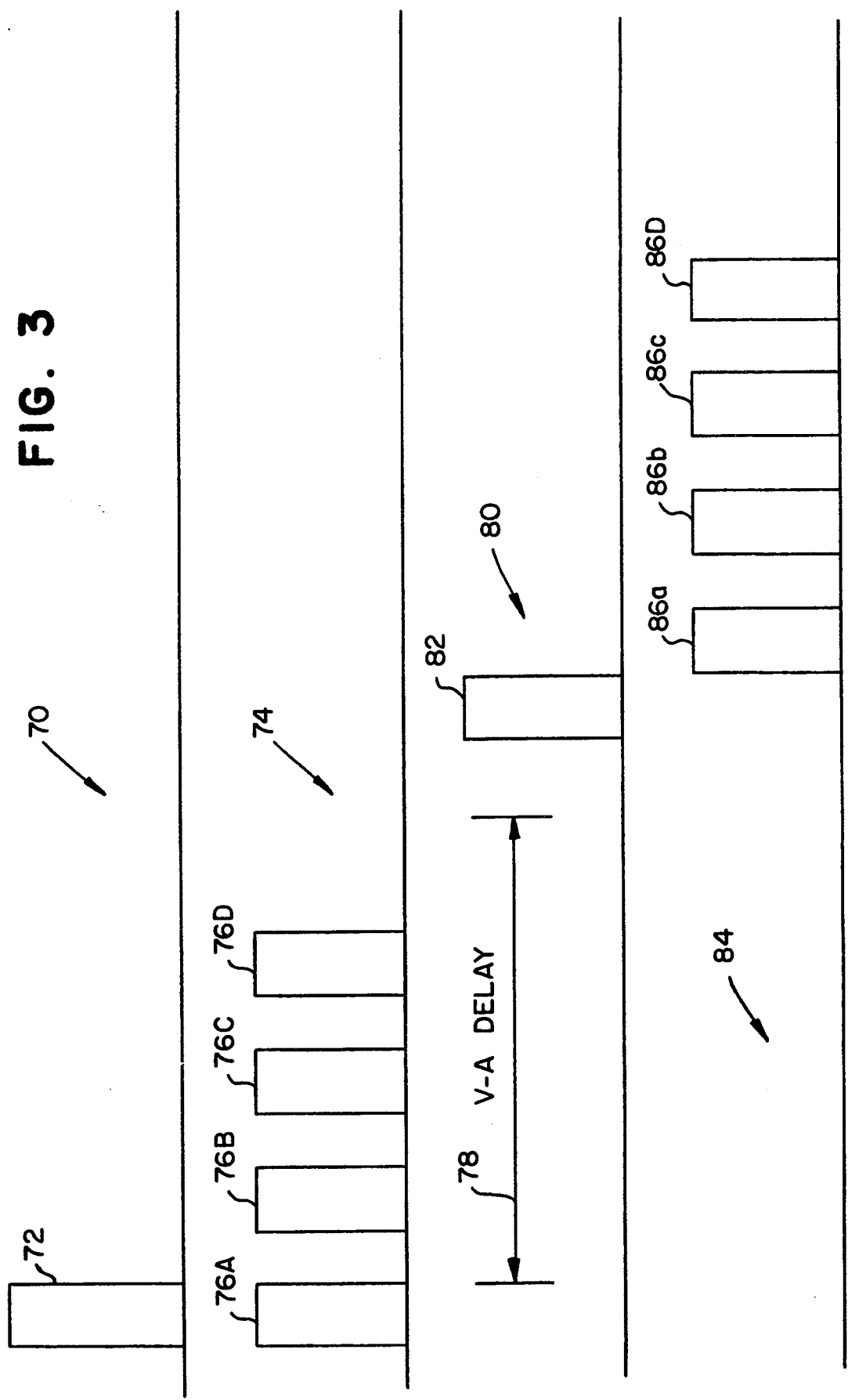

MUSCLE POWERED CARDIAC ASSIST SYSTEM

CROSS REFERENCE TO CO-PENDING APPLICATIONS

This is a continuation of co-pending U.S. patent application Ser. No. 07/597,316, filed Oct. 15, 1990, now U.S. Pat. No. 5,205,810. This application is related to U.S. Ser. No. 07/446,594, filed Dec. 6, 1989, entitled "Steroid Eluting Intramuscular Lead," now U.S. Pat. No. 5,009,229; U.S. Ser. No. 07/446,593, filed Dec. 6, 1989, entitled "Muscle Fitness Detection by Colorimetry," now U.S. Pat. No. 5,067,960; U.S. Ser. No. 07/446,592, filed Dec. 5, 1989, entitled "Muscle Work Output Monitor by Intramuscular Temperature Variation Measurement," now U.S. Pat. No. 5,089,019; and U.S. Ser. No. 07/446,811, filed Dec. 6, 1989, entitled "Muscle Contraction Control by Intramuscular Pressure Monitoring," now U.S. Pat. No. 5,098,442.

BACKGROUND OF THE INVENTION

1. Field of the Invention

The present invention relates generally to implantable cardiac assist systems, and more particularly, relates to implantable cardiac assist systems which are powered by a skeletal muscle of the patient.

2. Description of the Prior Art

The earliest cardiac assist systems were mechanical devices which move blood using an artificially powered pump. The two greatest disadvantages of such mechanical pumps relate to materials and energy sources. Material problems arise when artificial materials which are foreign to the body cause thrombosis after coming in contact with the blood. Much research is currently ongoing in an attempt to find materials which are more compatible with the blood. Yet the use of thrombogenic materials remains a major disadvantage of cardiac assist systems using mechanical pumps.

A second major disadvantage of mechanical pumps resides in the energy systems. Current energy storage systems in the form of batteries are simply not practical. With present day technology, the energy density and the capacity of implantable batteries limits the useful life of the battery. With percutaneous or radio frequency recharge, the energy stored corresponds to a few hours up to a day. However, this ordinarily leads to undue risk of infection.

The most promising solution to the energy aspect is to use a biochemical power source such as a muscle. Wrapping the skeletal muscle around the heart seems to resolve the issues around the materials problems. Because the blood touches only naturally endothelialized tissue, thrombogenic problems are eliminated. Because the vascularization of the skeletal muscle is preserved, power is derived from normal biological oxidation reactions.

U.S. Pat. No. 4,411,268 issued to Cox and U.S. Pat. No. 4,813,952 issued to Khalafalla, both of which are incorporated herein by reference, teach skeletal muscle powered cardiac assist systems. Even though such cardiac assist systems are known in the art, the prior art systems do not specifically provide atrio-ventricular synchrony (i.e., either natural or stimulated synchrony with a skeletal muscle boost).

SUMMARY OF THE INVENTION

The present invention provides a skeletal muscle powered cardiac assist system which can provide assistance to the right, as well as the left, side of the heart. It also ensures that the hemodynamic benefits of atrial filling are similarly assisted.

Right heart boost is important to ensure adequate pulmonary function in a patient experiencing atrial myocardial disease. Sufficient pulmonary pressure is necessary to provide the efficient oxygenation required by a patient previously weakened by hemodynamic deficiency.

Similarly, skeletal muscle assistance to the atria ensures that even with very ineffective myocardial tissue, sufficient atrial kick is present to offer the hemodynamic improvement associated with optimal ventricular filling.

The present invention provides these advantages by surgically dividing the harvested skeletal muscle into two separately stimulatable contractile components, or two separate skeletal muscles. The first is used to assist the atria, and the second assists the ventricles. Stimulation of the ventricular component is synchronized with contractions of the ventricles whether naturally or artificially paced. Similarly, the atrial component is stimulated to contract in proper synchrony with naturally or artificially paced atrial contractions.

BRIEF DESCRIPTION OF THE DRAWINGS

Further objects and advantages of the present invention will be apparent as the same becomes better known from the detailed specification and accompanying drawings in which like reference numerals refer to like components and wherein:

FIG. 3 is a timing diagram for the pulses produced by the implantable pulse generator of the present invention.

DETAILED DESCRIPTION OF THE PREFERRED EMBODIMENTS

Figure 1A:
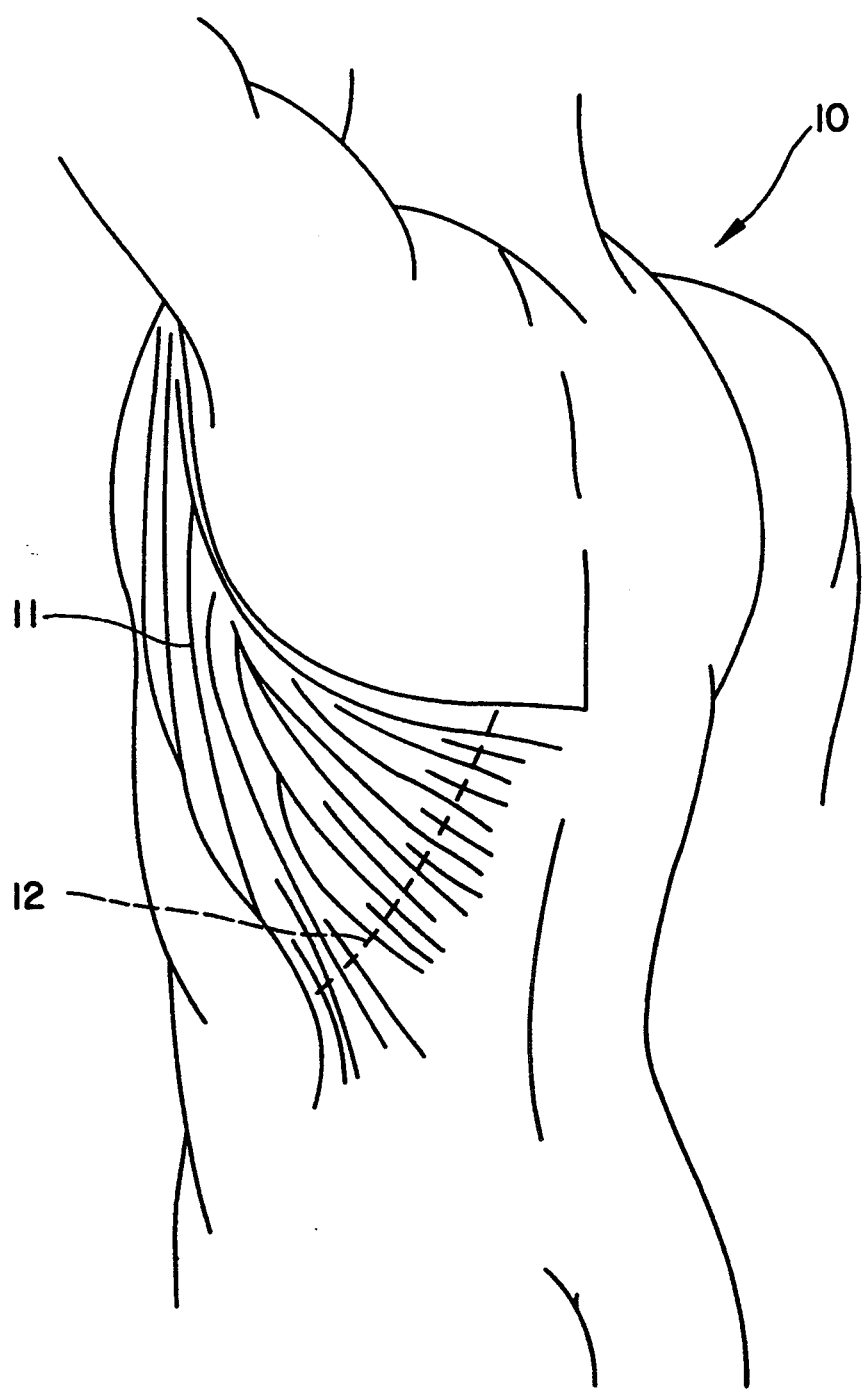
FIG. 1A is a left side view of a patient showing the location of skeletal muscle to be used for cardiac assist.

FIG. 1A is a left side view of a patient 10 showing the initial location of the skeletal muscle 11 to be used to power the cardiac assist system of the present invention. Use of the left latissimus dorsi is shown by way of example only and is not intended to limit the present invention. Other skeletal muscles may also be used.

Shown schematically is the line of incision 12 for severing skeletal muscle 11 from its initial position. Notice that skeletal muscle 11 is severed posteriorly and inferiorally to preserve maximum innervation and vascularization.

Figure 1B:
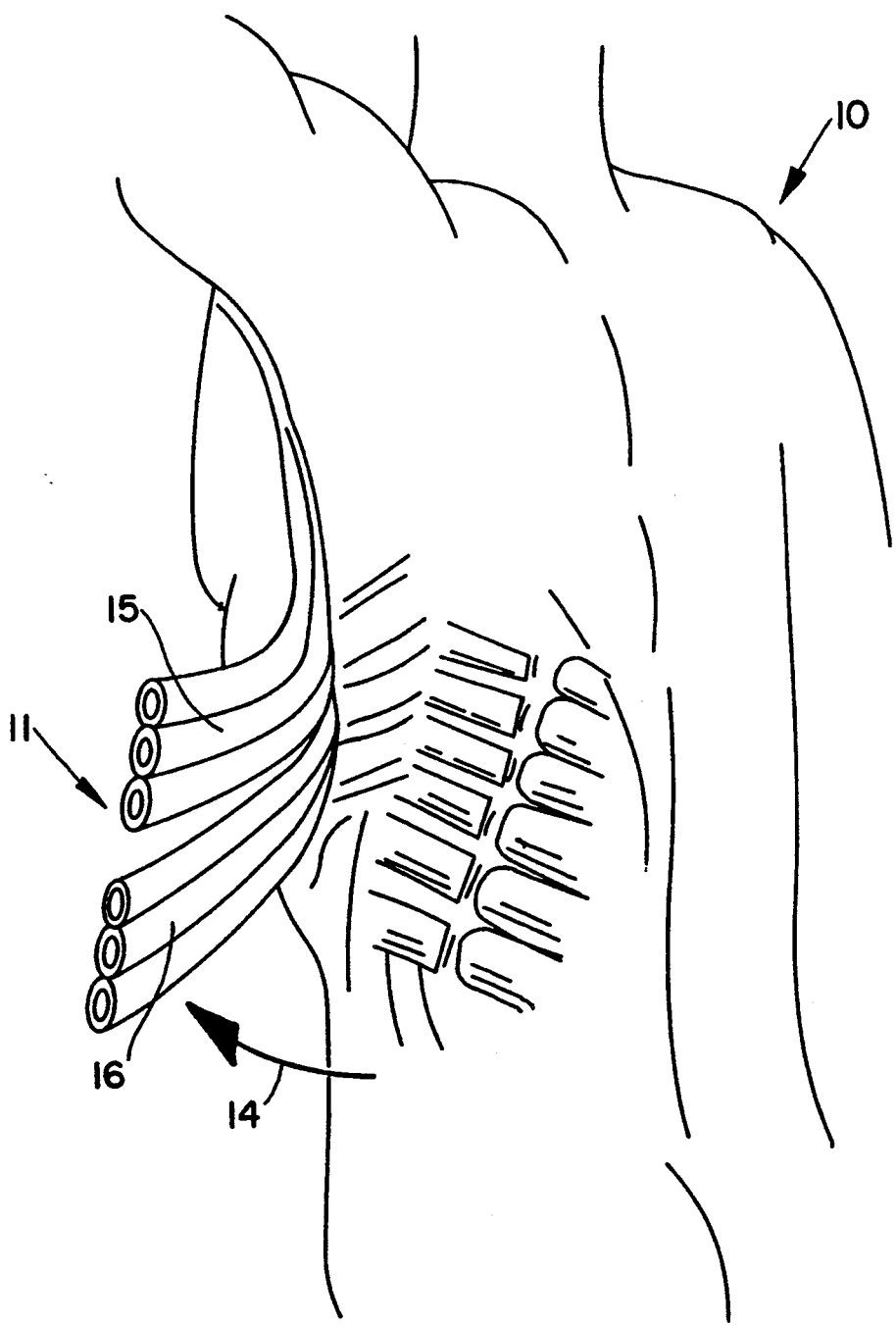
FIG. 1B is a view similar to FIG. 1A with the skeletal muscle severed posteriorly.

FIG. 1B is a similar view of patient 10 with skeletal muscle 11 severed at line of incision 12 (see also FIG. 1A). After being severed, skeletal muscle 11 is carefully elevated in the direction of arrow 14. At this time, skeletal muscle 11 is separated into an upper component 15 and a lower component 16. It is important to separate skeletal muscle 11 while still preserving the maximum innervation and vascularization.

Figure 1C:
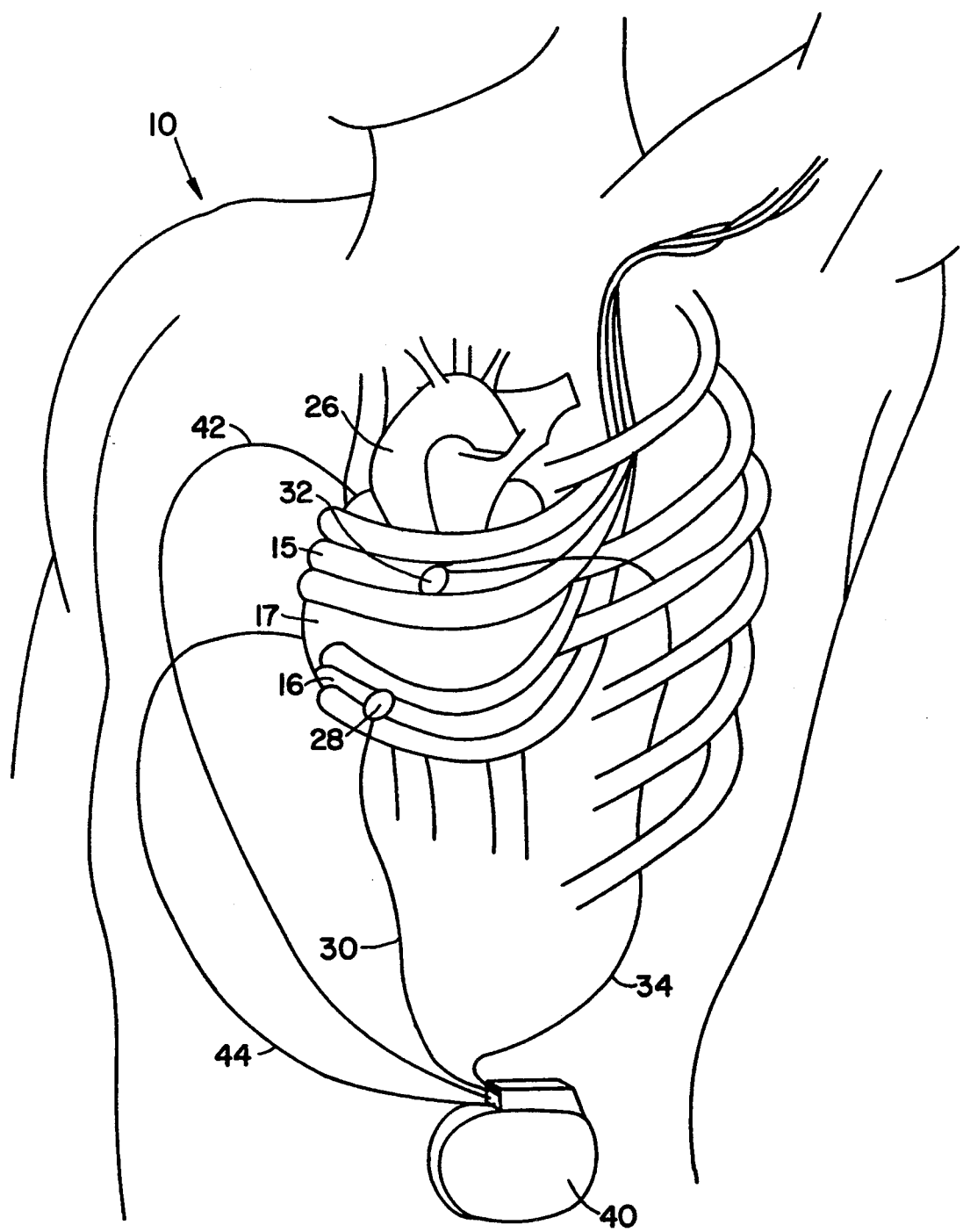
FIG. 1C is a front view of a patient's thorax after completion of the implant, but before closure.

FIG. 1C is a front view of patient 10 showing upper component 15 wrapped about both right and left atria of heart 17, and lower component 16 wrapped about both right and left ventricles of heart 17. The free ends of upper component 15 and lower component 16 are fixedly attached in the manner known in the art.

Implantable pulse generator 40 is implanted in a convenient place, such as the lower abdomen.

As shown, both components may be harvested from the latissimus dorsi, although other skeletal muscles may be used. Each is prepared and conditioned in accordance with the teaching of U.S. Pat. No. 4,411,268 issued to Cox. Upper component 15 is stimulated to contract by electrode 32 which is coupled to the implantable pulse generator 40 via insulated lead 34. Similarly, electrode 28, which is coupled to the implantable pulse generator 40 by insulated lead 30, stimulates contractions in lower component 16. Heart 17 may be artificially paced transvenously through superior vena cava 26 in accordance with one or more of the accepted pacing modalities, or epicardially in accordance with one or more accepted pacing modalities. Atrial and ventricular sensing and stimulation are accomplished using epicardial leads 42 and 44, respectively.

Figure 1D:
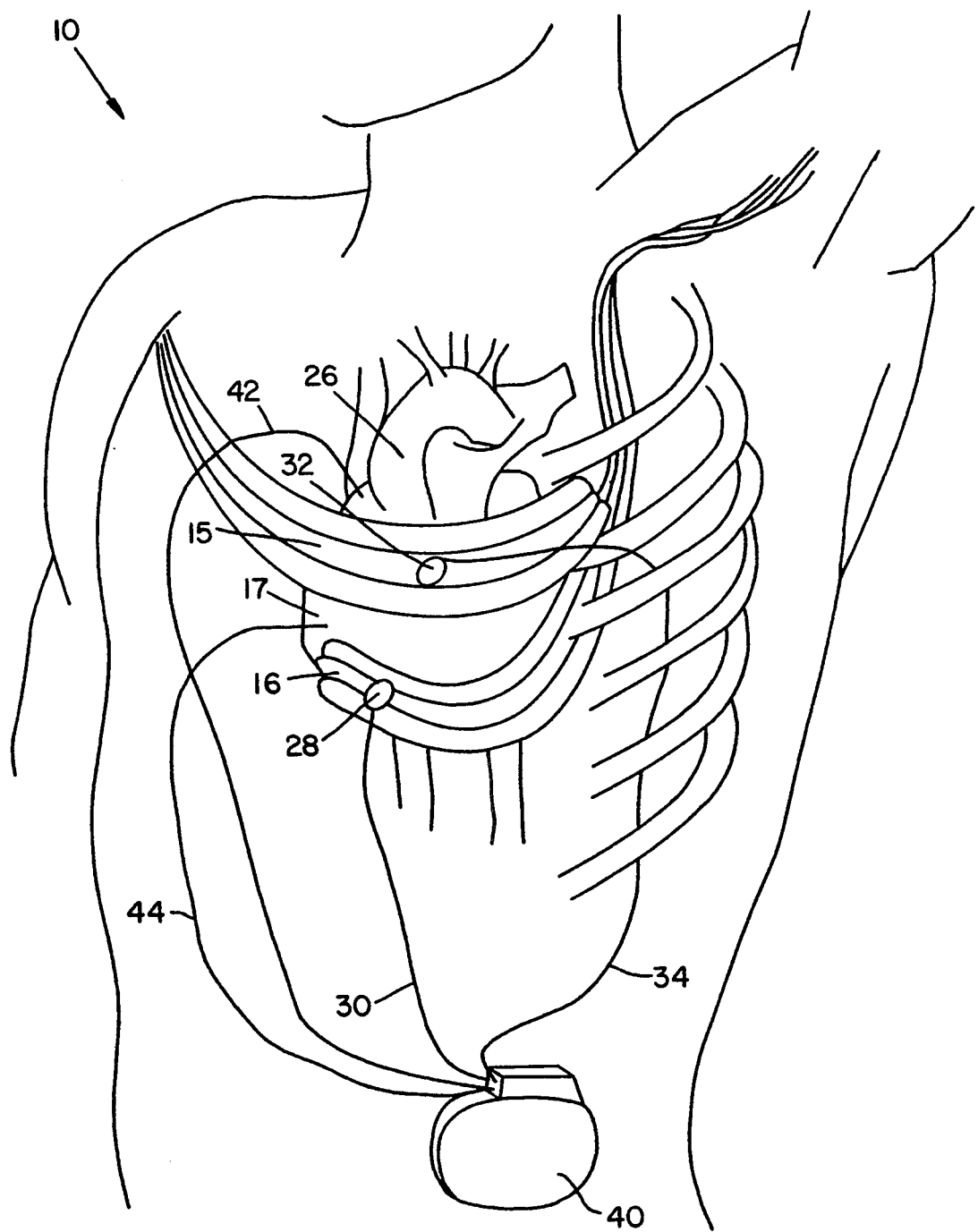
FIG. 1D is a view similar to FIG. 1C of an alternative embodiment.

FIG. 1D is a view similar to that of FIG. 1C. However, in this embodiment, upper component 15 is taken from the right latissimus dorsi and lower component 16 is taken from the left latissimus dorsi. All other elements are as previously described.

Figure 2A:
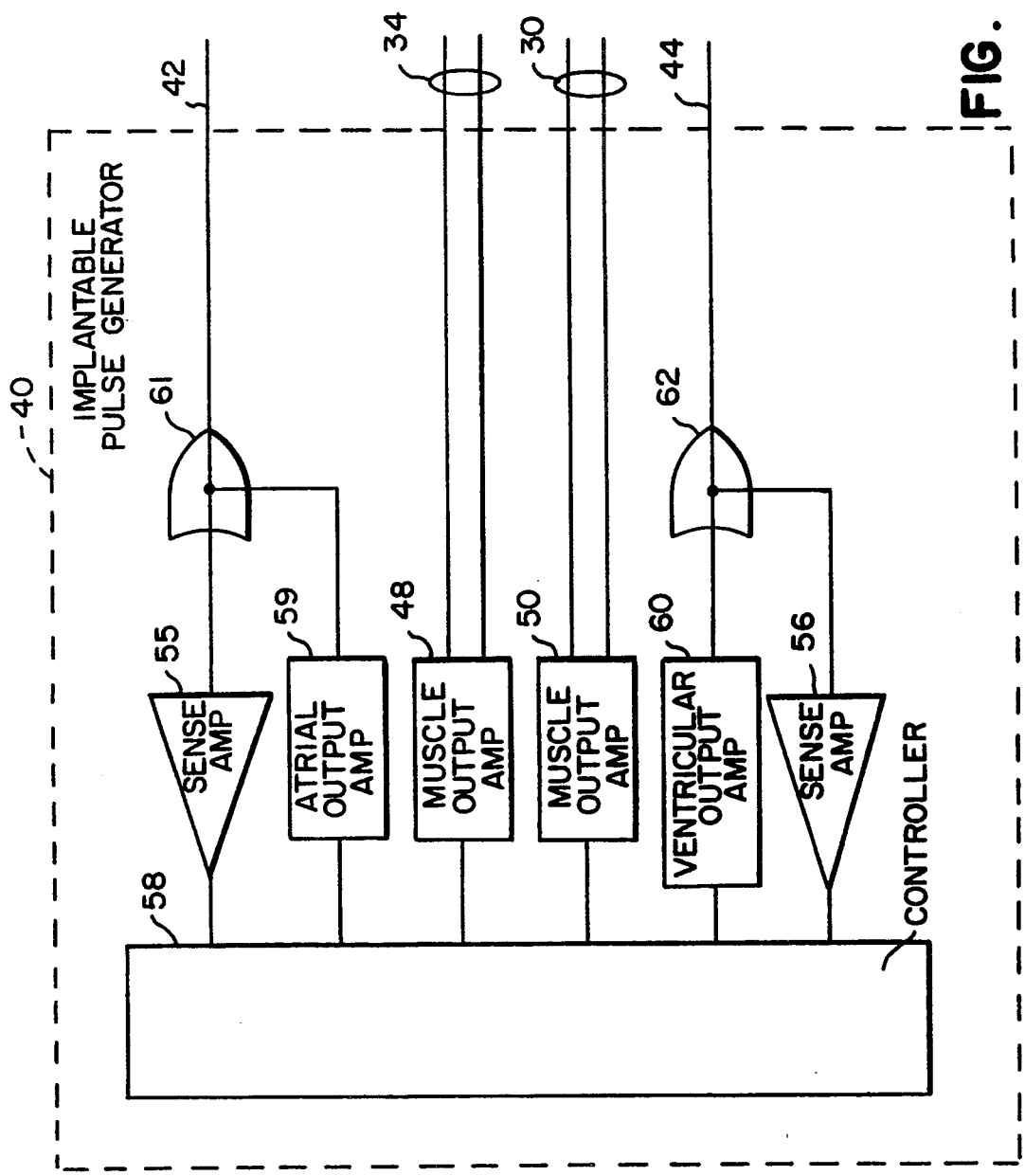
FIG. 2A is a block diagram for the implantable pulse generator of the present invention.

FIG. 2A is a block diagram of the preferred mode of implementing implantable pulse generator 40. In the preferred mode, the circuitry is microprogrammable, although hardwired embodiments are also useful. The microprogrammed architecture is the most flexible in that it can be programmed to operate in any of the ICHD modes and others not yet defined. Preferably, implantable pulse generator 40 operates in the DDD mode as described in U.S. Pat. No. 4,312,355, issued to Funke, herein incorporated by reference.

In the DDD mode, the pacer senses the ventricle for naturally occurring ventricular contractions. If such a contraction is not sensed within the predetermined (and programmable) escape interval, an artificial pacing pulse is supplied to the right ventricle. If a natural contraction is sensed, the artificial pacing pulse to the ventricle is inhibited. In either case, the atrium is next sensed. Again, an artificial pacing pulse is supplied to the atrium if a natural contraction is not sensed within the escape interval.

Controller 58 is a microprocessor which is microprogrammed to provide the desired timing and logic to implement the chosen modality. As described above, the DDD mode is preferred. Atrial pacing lead 42 supplies electrical coupling between the atrium and sense amplifier 55 and atrial output amplifier 59 via wired or circuit 61. Similarly, ventrical pacing lead 44 supplies electrical coupling between the ventricles and ventricular output amplifier 60 and sense amplifier 56 via wired or circuit 62. The skeletal muscle masses are stimulated by muscle output amplifier 48 and muscle output amplifier 50 via leads 34 and 30, respectively.

FIG. 3 is a graphical representation of the output of implantable pulse generator 40 for one typical cardiac cycle. Graph 70 shows the presence of a ventricular contraction as pulse 72. In this case the ventricular contraction is artificially stimulated by pulse 72 as produced by ventricular output amplifier 60. This pulse is as measurable on pacing lead 44.

Graph 74 shows the resulting output of muscle output amplifier 50. In the preferred mode, stimulation of the lower component 16 is accomplished by a burst of four pulses comprising pulses 76a, 76b, 76c, and 76d.

Graph 80 shows the atrial stimulation pulse 82 generated by atrial output amplifier 59 or 146 following the end of the atrial escape period because a naturally occurring atrial contraction is not sensed. As explained above, this v-a delay (78 in FIG. 3) can be measured from the sensed or artificially stimulated ventricular event.

Graph 84 shows the burst of pulses generated by muscle output amplifier 48 or 148. This burst consists of the four pulses 86a, 86b, 86c, and 86d.

Having thus described the preferred mode of the present invention, those of skill in the art will be readily able to apply the teaching found herein to various other skeletal muscle powered cardiac assist systems without deviating from the scope of the claims hereto attached.

What is claimed is:

1. A cardiac assist system operatively coupled to a first skeletal muscle mass wrapped about the atria of a heart and a second skeletal muscle mass wrapped about the ventricles of the heart, said system comprising:
   a. contraction detection means coupled to said atria and said ventricles for detecting contractions of said atria and said ventricles; and
   b. stimulation means coupled to said contraction detection means and adapted to be coupled to said first and second skeletal muscle masses for stimulating said first skeletal muscle mass to contraction in response to the detection of an atrial contraction, and for stimulating said second skeletal muscle mass to contraction in response to the detection of a ventricular contraction.

2. The cardiac assist system according to claim 1 wherein the stimulation of said first skeletal muscle is at a predetermined interval after the stimulation of said second skeletal muscle mass.

3. A cardiac assist system according to claim 1 wherein said stimulation means is operatively coupled to said ventricles, and said stimulation means stimulates said ventricles to contraction.

4. A cardiac assist system according to claim 2 wherein said stimulation means is operatively coupled to said ventricles, and said stimulation means stimulates said ventricles to contraction.

* * * * *